(12) United States Patent
Beckers et al.

(10) Patent No.: US 11,915,821 B2
(45) Date of Patent: Feb. 27, 2024

(54) CLOUD-BASED RADIOLOGY COMMENTING AND WORKSPACE SHARING

(71) Applicant: Arterys Inc., San Francisco, CA (US)

(72) Inventors: Fabien Rafael David Beckers, San Francisco, CA (US); John Axerio-Cilies, Berkeley, CA (US); Maud Josee Caroline Benaddi, London (GB); Patrick Ross Corless, Calgary (CA); Shek Bun Law, Calgary (CA); Justin Reid, Calgary (CA); Derek John Scherger, Calgary (CA); Kendall Wu, Mountain View, CA (US)

(73) Assignee: ARTERYS INC., San Francisco, CA (US)

( * ) Notice: Subject to any disclaimer, the term of this patent is extended or adjusted under 35 U.S.C. 154(b) by 56 days.

(21) Appl. No.: 17/286,128

(22) PCT Filed: Nov. 19, 2019

(86) PCT No.: PCT/US2019/062230
§ 371 (c)(1),
(2) Date: Apr. 16, 2021

(87) PCT Pub. No.: WO2020/106729
PCT Pub. Date: May 28, 2020

(65) Prior Publication Data
US 2021/0383914 A1   Dec. 9, 2021

Related U.S. Application Data

(60) Provisional application No. 62/770,051, filed on Nov. 20, 2018.

(51) Int. Cl.
*G16H 10/60* (2018.01)
*G06F 21/60* (2013.01)
(Continued)

(52) U.S. Cl.
CPC ........... *G16H 30/20* (2018.01); *G06F 21/602* (2013.01); *G06F 40/169* (2020.01); *G16H 30/40* (2018.01); *G16H 40/20* (2018.01); *G16H 10/60* (2018.01)

(58) Field of Classification Search
CPC ........ G16H 30/20; G16H 10/60; G16H 30/40; G16H 40/20
See application file for complete search history.

(56) References Cited

U.S. PATENT DOCUMENTS

| 2008/0021741 A1 | 1/2008 | Holla et al. |
| 2008/0212855 A1 * | 9/2008 | Shibuya ................. G16H 30/20 |
| | | 382/128 |

(Continued)

FOREIGN PATENT DOCUMENTS

| CN | 103838813 A | 6/2014 |
| JP | WO2012/049741 A1 | 4/2012 |

(Continued)

OTHER PUBLICATIONS

International Search Report and Written Opinion, dated Mar. 16, 2020, for International Application PCT/US2019/062230, 9 pages.
(Continued)

*Primary Examiner* — Jay M. Patel
(74) *Attorney, Agent, or Firm* — Seed IP Law Group LLP (57) ABSTRACT

This disclosure relates to a medical image viewer for incorporating multi-user collaboration features, such as in-image commenting and workspace sharing. An example method includes receiving a comment location including image coordinates and comment information associated with the comment from a user device. The comment information includes a text body, identify identity information related to the user, and a comment creation date. The example method further includes determining world coordinates based on the image coordinates, and storing the world coordinates and the
(Continued)

comment information as a subset of header attributes of the DICOM image file.

16 Claims, 8 Drawing Sheets

(51) Int. Cl.
*G06F 40/169* (2020.01)
*G16H 30/20* (2018.01)
*G16H 30/40* (2018.01)
*G16H 40/20* (2018.01)

(56) References Cited

U.S. PATENT DOCUMENTS

| | | |
|---|---|---|
| 2010/0135552 A1 | 6/2010 | Leib et al. |
| 2013/0141366 A1* | 6/2013 | Ritter ............... G06F 3/041 345/173 |
| 2014/0143298 A1 | 5/2014 | Klotzer et al. |
| 2014/0172457 A1* | 6/2014 | Ueda ............... G16H 30/40 705/3 |
| 2014/0243684 A1 | 8/2014 | Curiel et al. |
| 2014/0267662 A1 | 9/2014 | Lampo |
| 2015/0123769 A1* | 5/2015 | Dalal ............... A61B 34/10 340/8.1 |
| 2015/0278385 A1 | 10/2015 | Tolle et al. |
| 2015/0278446 A1 | 10/2015 | Tolle et al. |
| 2017/0124771 A1 | 5/2017 | Canfield et al. |
| 2018/0060533 A1 | 3/2018 | Reicher et al. |
| 2018/0182494 A1 | 6/2018 | Lampo |
| 2018/0189255 A1 | 7/2018 | Kofman et al. |
| 2019/0182454 A1* | 6/2019 | Berger ............... H04N 7/148 |
| 2020/0176104 A1 | 6/2020 | Taniguchi et al. |

FOREIGN PATENT DOCUMENTS

| | | |
|---|---|---|
| JP | 2012-221365 A | 11/2012 |
| JP | 2018-529475 A | 10/2018 |
| KR | 10-1534272 B1 | 7/2015 |
| WO | WO 2015166377 A1 | 11/2015 |
| WO | WO 2017060791 A1 | 4/2017 |
| WO | 2017/163384 A1 | 9/2017 |
| WO | 2018/136954 A1 | 7/2018 |

OTHER PUBLICATIONS 12.5 DICOM Data and Coordinates, URL=https://mevislabdownloads.mevis.de/docs/current/MeVisLab/Resources/Documentation/Publish/SDK/GettingStarted/ch12s05.html, download date May 16, 2022, 2 pages.
Extended European Search Report, dated May 20, 2022, for European Application No. 19887496.8-1126, 16 pages.
Office Action, dated Aug. 30, 2023, for Chinese Patent Application No. 201980076239.8. (12 pages)(with English Translation).
Search Report, dated Aug. 25, 2023, for Chinese Patent Application No. 201980076239.8. (9 pages)(with English Translation).
Japanese Office Action, dated Dec. 26, 2023, for Japanese Patent Application No. 2021-526652. (12 pages) (with English Translation).

* cited by examiner

CLOUD-BASED RADIOLOGY COMMENTING AND WORKSPACE SHARING

CROSS-REFERENCE TO RELATED APPLICATION(S)

This application claims the benefit of priority to U.S. Provisional Application No. 62/770,051, filed Nov. 20, 2018, which application is hereby incorporated by reference in its entirety.

BACKGROUND

Technical Field

This disclosure relates generally to medical imaging applications, and, more particularly, to a medical image viewer for incorporating multi-user collaboration features, such as in-image commenting and workspace sharing.

Description of the Related Art

Radiology images usually consist of two-dimensional images, three-dimensional images, or reconstructed fused images generated through imaging equipment utilizing modern nuclear medicine techniques, for example, positron emission tomography (PET), computed tomography (CT), magnetic resonance imaging (MRI), functional MRI (fMRI), X-ray, mammography, tomosynthesis, ultrasound or other modalities. Radiological images are generally saved in a patient's medical records (e.g., an electronic medical record or EMR), an electronic health record (EHR), or a Picture Archiving and Communication System (PACS), which images may be viewed by the patient or health professionals in the course of rendering diagnosis, treatment, or other health care. However, communication pertaining to radiological images can be insecure, inefficient, and/or limited in urgent situations. Users may share logins and passwords, use handwritten notes, create CDs, or call other users to communicate vital, sometimes time-sensitive information about specific features in a radiological image.

Modern EMR and EHR software systems and PACS provide some communication facilities between providers and patients. However, radiological images shared through these channels may lack diagnostic information generated in the course of a radiological physician's survey. Even in cases where diagnostic metadata is provided, physicians are unable to communicate rich feature data, e.g., location, measurements, and are unable to continue conversations nor collaborate with other physicians or their patients. One example is Horos, which provides cloud sharing with other users, but no facility for conversation nor collaboration.

Radiology images generally follow the Digital Imaging and Communications in Medicine (DICOM) standard, which sets the file/data format, data interchange protocol and network protocol architecture used for digital radiology imaging. The DICOM standard plays a prominent role in the emergence of Picture Archiving and Communication Systems (PACS) which integrate with hospital information systems (HIS) and radiology information systems (RIS).

As adoption of digital imaging at an enterprise level grows, so will the demand for not only streamlined communication, but also collaboration. Using current imaging applications, radiology professionals are unable to collaborate on imaging studies with other healthcare professionals who lack the necessary equipment or software to provide cogent, feature-specific feedback in a timely manner. Though digital radiology imaging applications provide sophisticated toolsets and viewing environments, they fail to facilitate collaboration in certain situations, for example, longitudinal studies involving comprehensive collections of digital images and annotations made thereto.

Current PACS do not provide the precision required to share persistent diagnostic information nor collaborate in digital image viewing environments. Thus, there exists a need for a PACS which provides communication and collaboration tools accessible across platforms and geographical areas.

BRIEF DESCRIPTION OF THE DRAWINGS

The embodiments of this disclosure are illustrated by way of example and not limitation in the figures of the accompanying drawings, in which like references indicate similar elements and in which.

Other features of the present embodiments will be apparent from the accompanying drawings and from the detailed description that follows.

DETAILED DESCRIPTION

Various applications, methods and systems are disclosed herein to provide improved communication and collaboration for digital radiology imaging environments. The described embodiments may facilitate storing comments within a digital biomedical image (hereinafter "image") in accordance with one or more communication standards, such as the DICOM 3.X standard. It will be appreciated that the disclosed embodiments are applicable to future standards, i.e., updates to the DICOM standard or other standards altogether. The described embodiments may also facilitate the sharing of a workspace within a digital biomedical image viewing application with other users. Such embodiments may employ a cloud-based software application configured to, inter alia, interpret and display DICOM image data without requiring an end-user to locally store image data or metadata.

Figure 1:
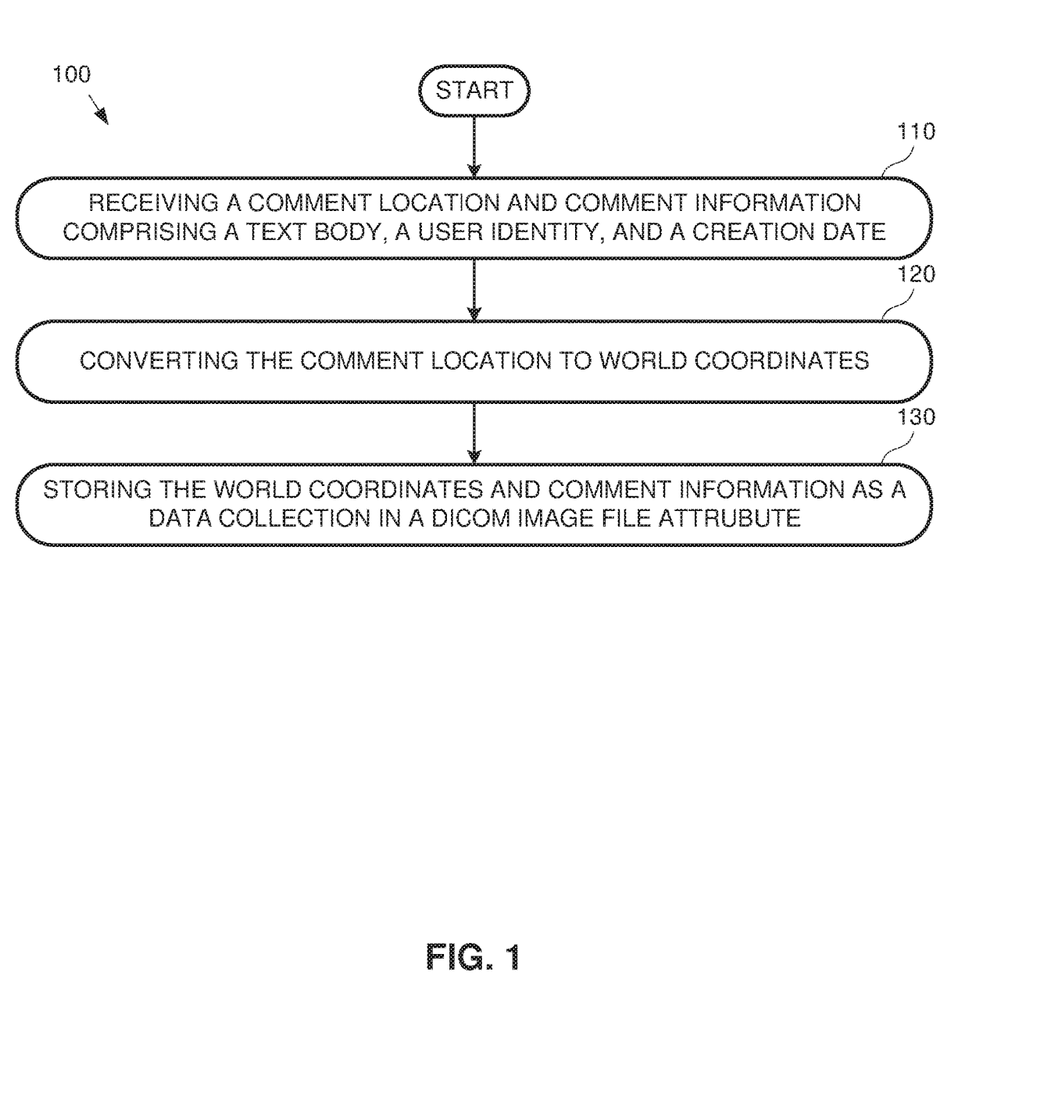
FIG. 1 shows an exemplary method of creating and storing one or more comments within a DICOM image file, according to one or more embodiments.

Referring to FIG. 1, an exemplary method 100 of creating and storing one or more comments within a DICOM image file is illustrated. As shown, the method 100 begins at step 110, in which a viewer system receives a comment location and comment information from a user. Said user may access the viewer system through a thin client device (user device), which user device comprises processing and storage hardware and is configured to execute a viewer application accessible via an Internet or intranet application stored thereon.

Figure 2:
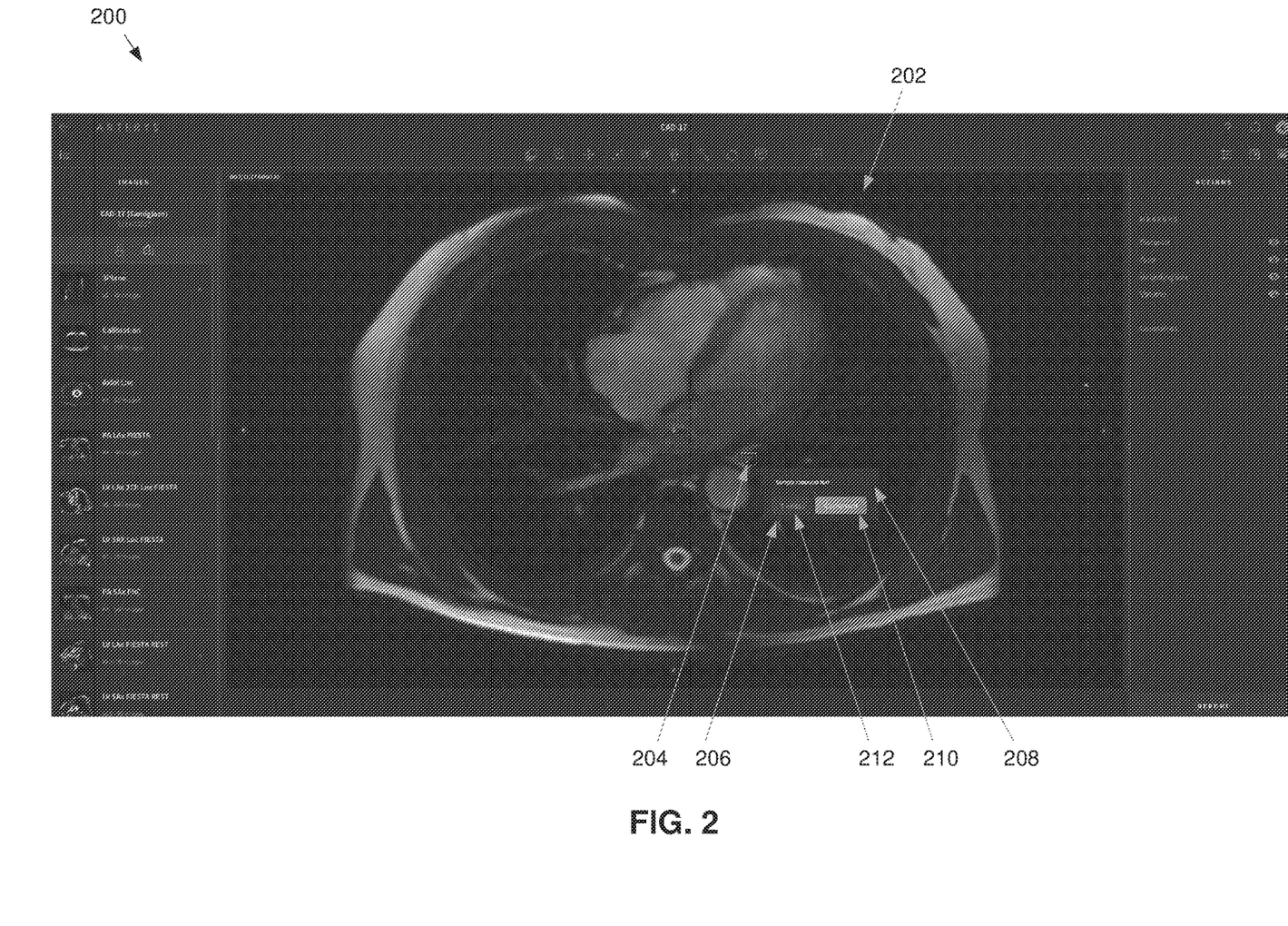
FIG. 2 shows an exemplary workspace for placing comments on a DICOM image file.

Referring to FIG. 2, a workspace 200 for placing comments is illustrated. In one or more embodiments, the viewer system may allow a user to create, store, and share a workspace, e.g., workspace 200. As used herein, 'workspace' refers to a user-configured collection of DICOM image files related to one or more studies and one or more user interface(s) configurable by the viewer application to enable collaboration. The collection of DICOM image files, the comments, the annotations may all be attributes of the workspace which may be configurable by a user. Accordingly, workspaces may include annotations, comments, visual analytics, patient demographic information, or any other toolsets relevant to a study. Any such configuration of the workspace may be stored in a memory of the viewer system as described below.

In one embodiment, the user selects, through a workspace 200 of a viewer application executed by a data processing device (user device) of the user, a location on a DICOM image 202 received from a viewer system through a network and displayed through the viewer application as shown. Once a location is selected, a short-form of the comment, i.e., an icon 204, is displayed at the image coordinates associated with the location. Also, a user interface window 206 may popup to prompt the user to input a text body 208 and subsequently select whether to place a comment ("comment" button 210) or cancel placement ("cancel" button 212).

Comment information comprises a text body, a user identity (e.g., email, first name, last name), and a creation date (e.g., a timestamp) generated by the viewer application at the time of comment creation. The user identity may be retrieved from the user's profile information which may be generated during a first login. In one embodiment, the text body may include alphanumeric characters. In a further embodiment, the text body may comprise HTML formatting elements.

Once the user submits the comment as described above, the viewer application transmits the comment information to the viewer system to be stored in persistent memory, e.g., non-volatile memory. The comment information stored in the memory of the user device may be subsequently removed. Accordingly, the viewer application may leave a limited footprint on the user device by depending on the computing power and storage provisions of the viewer system and third-party systems, such as HIS, RIS, and/or other PACS.

Referring back to FIG. 1, in a further step 120, the viewer system converts image coordinates to world coordinates. World coordinates may be converted back to image coordinates when the same image is viewed through another viewer application instance to display the comment at the location on the image.

A final step 130 involves storing the world coordinates and comment information within a value field of a DICOM attribute, such as a STUDY ID. The STUDY ID attribute may be a preferred embodiment because STUDY ID is a required element of any DICOM image file and is preserved within the DICOM standard as a modality-specific attribute, i.e., the STUDY ID is generated by the equipment and is used to identify the study for future reference and optionally carry study-related information. However, it will be appreciated that different header attributes or other elements of the DICOM image file, such as STUDY UID may be alternately or additionally employed to store comment information, including content, time of creation, user identities, and hierarchical relationships therebetween.

Additionally, image properties may also be stored along with the world coordinates and comment information. Image properties may include image metadata at the time of comment creation, for example, multiplanar reformation (MPR) properties, and may allow in-comment preservation of the image state prior to comment creation. Upon displaying a comment, the image properties associated therewith may also be applied. Accordingly, clicking a comment displays a snapshot of the image file at the time of comment creation. Sharing context in this way may reduce ambiguity and streamline communication.

Figure 3:
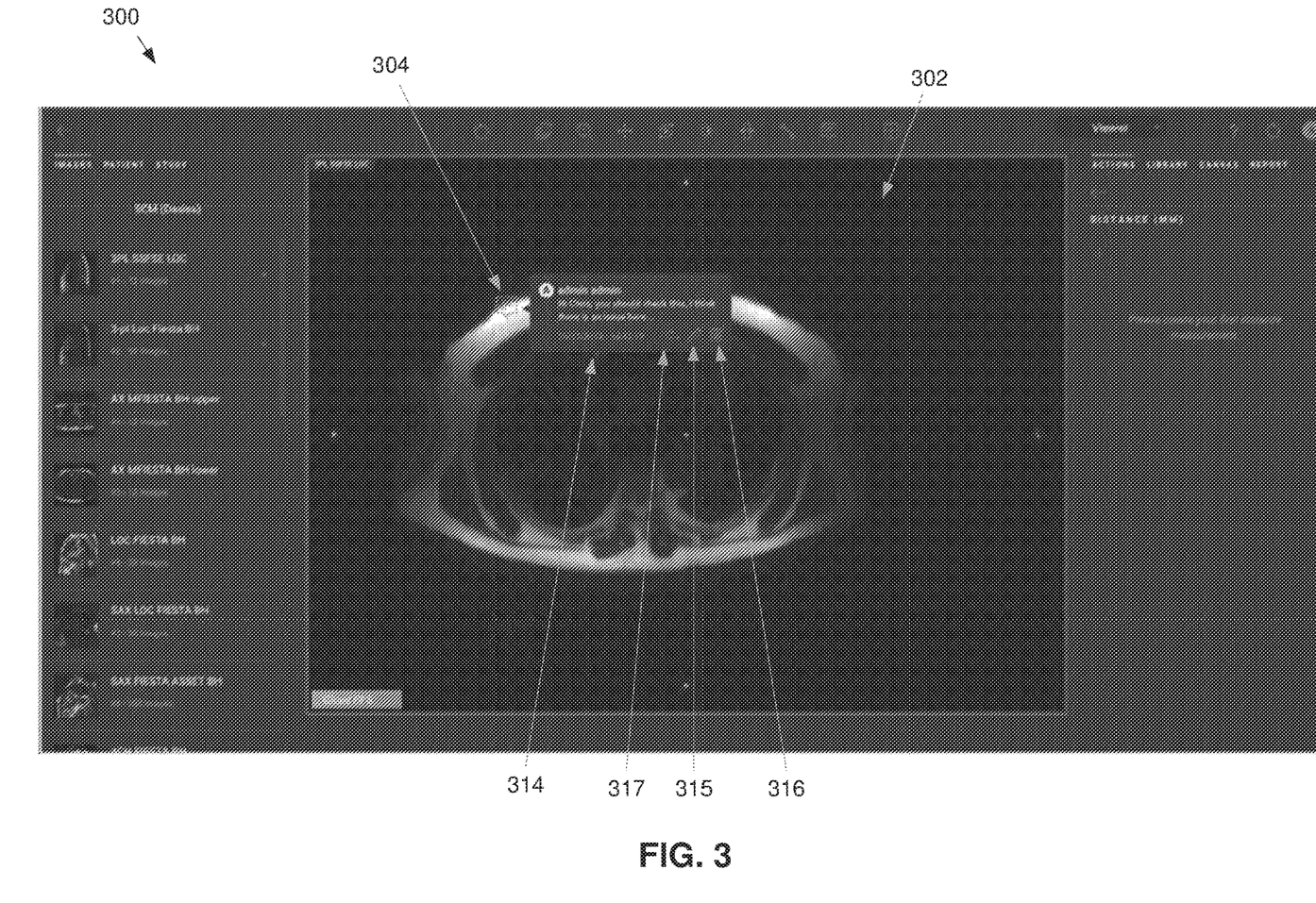
FIG. 3 shows an exemplary workspace displaying a placed comment.

Referring to FIG. 3, a workspace 300 showing a placed comment 314 is illustrated. The comment 314 may be viewable by other users through viewer applications of corresponding user devices. The comment 314 may display the user entity, the text body, and a date of creation. A delete button 316 may be provided to delete the comment. Clicking on the comment icon 304 may minimize the comment, i.e., hide the comment information and show only the comment icon. Subsequently clicking on the corresponding icon displays the comment again.

Figure 7:
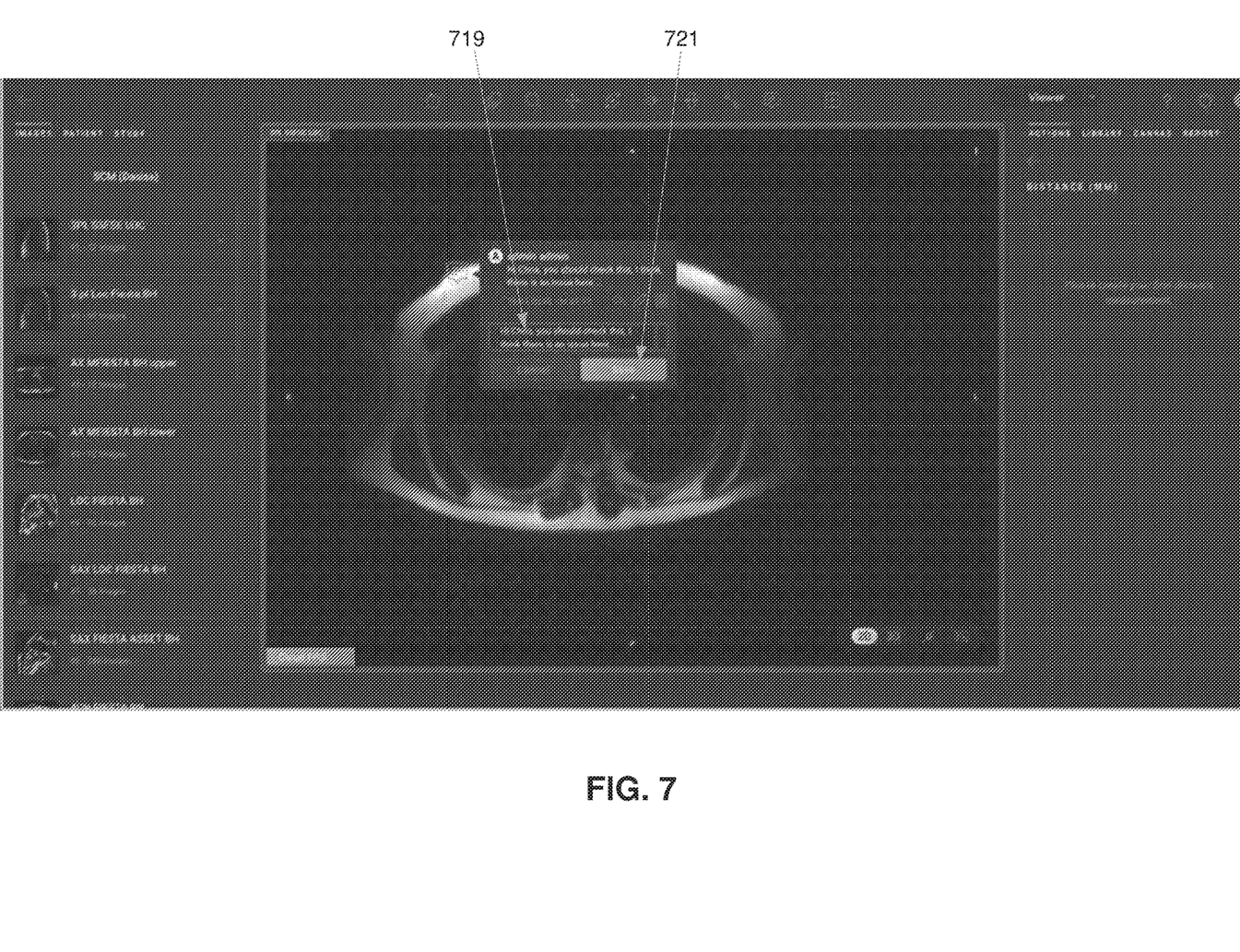
FIG. 7 shows a workspace demonstrating editing a comment.

In other embodiments, the comment window may further comprise one or more selectable actions, such as an 'edit' button 315 or a 'reply' button 317. Editing may be shown in FIG. 7. Choosing to edit may allow a user to modify the comment information, namely the text body 719. In some embodiments, the comment information may only be edited by a user having the same associated user identity information. In other embodiments, the original posting user may provide access to individual users or share the relevant workspace with other users within an organization to allow editing and/or reply to the comment. Or, the user may invite another organization or users thereof to collaborate. In one embodiment, editing may involve retrieving, by the user device, comment information from the viewer system, updating the comment information, and transmitting the updated comment information to the viewer system. Once the edit is complete, the user may select the 'save button' 721 to store the text body 719 in the viewer system (i.e., replace the comment information previously stored in the study ID).

Figure 8:
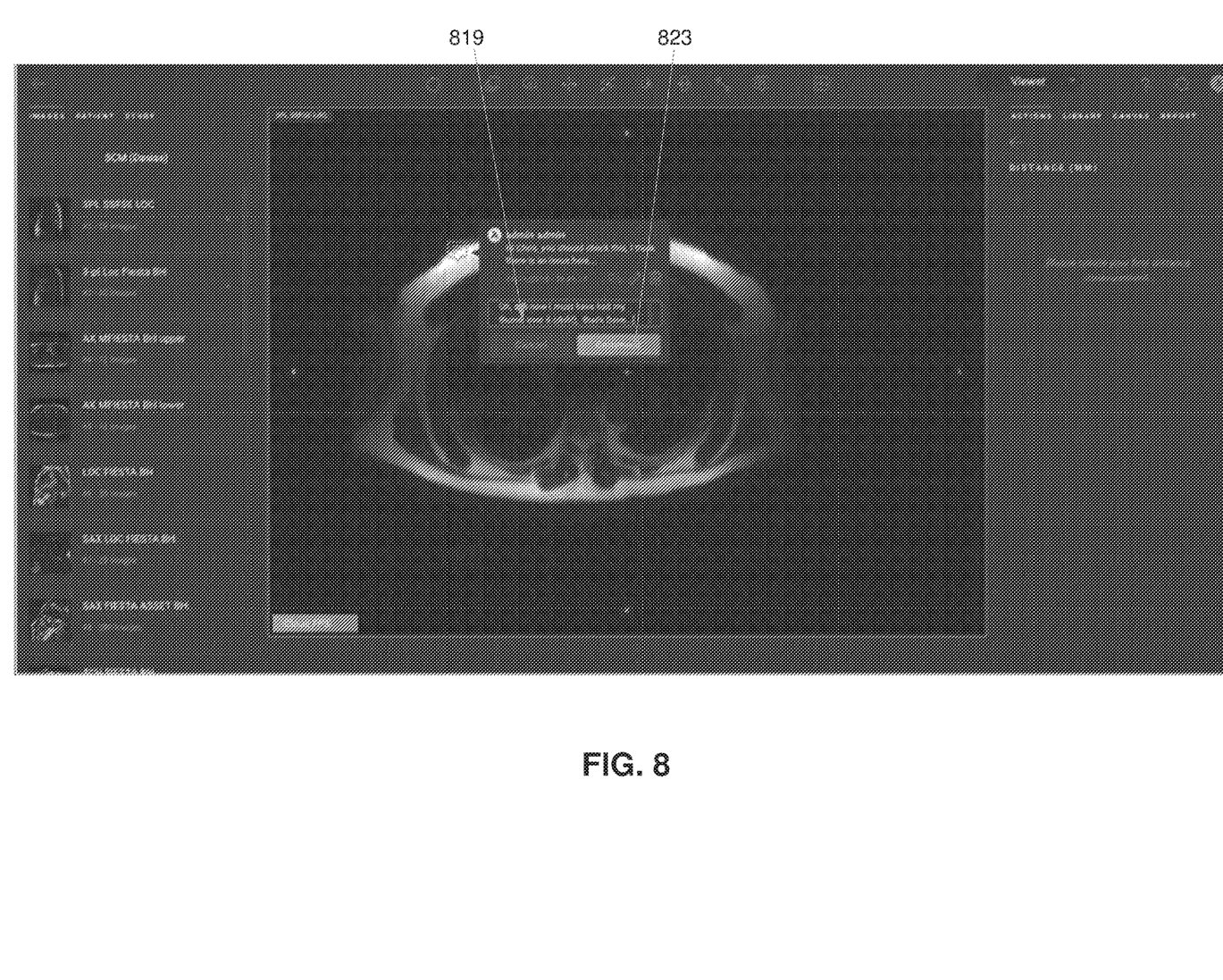
FIG. 8 shows a workspace demonstrating replying to a comment.

Replying to a comment may be shown in FIG. 8. The replying user may be prompted to enter a text body 819 and confirm the text body by selecting the 'comment' button 823 to store the reply in the comment information.

The reply function may utilize threading to store parent-child relationships between portions of a comment thread and enable conversations between professionals on a world coordinate-basis. A comment thread may comprise an original comment and one or more replies made thereto. The comment thread may be organized by date.

In some embodiments, the viewer application may display a list of one or more comments associated with a number of comment icons at any number of locations on an image. Once a comment icon is selected, the comment information associated with the comment icon may be viewed in a comment window generated substantially proximal to the location, as shown in FIG. 3.

Figure 4:
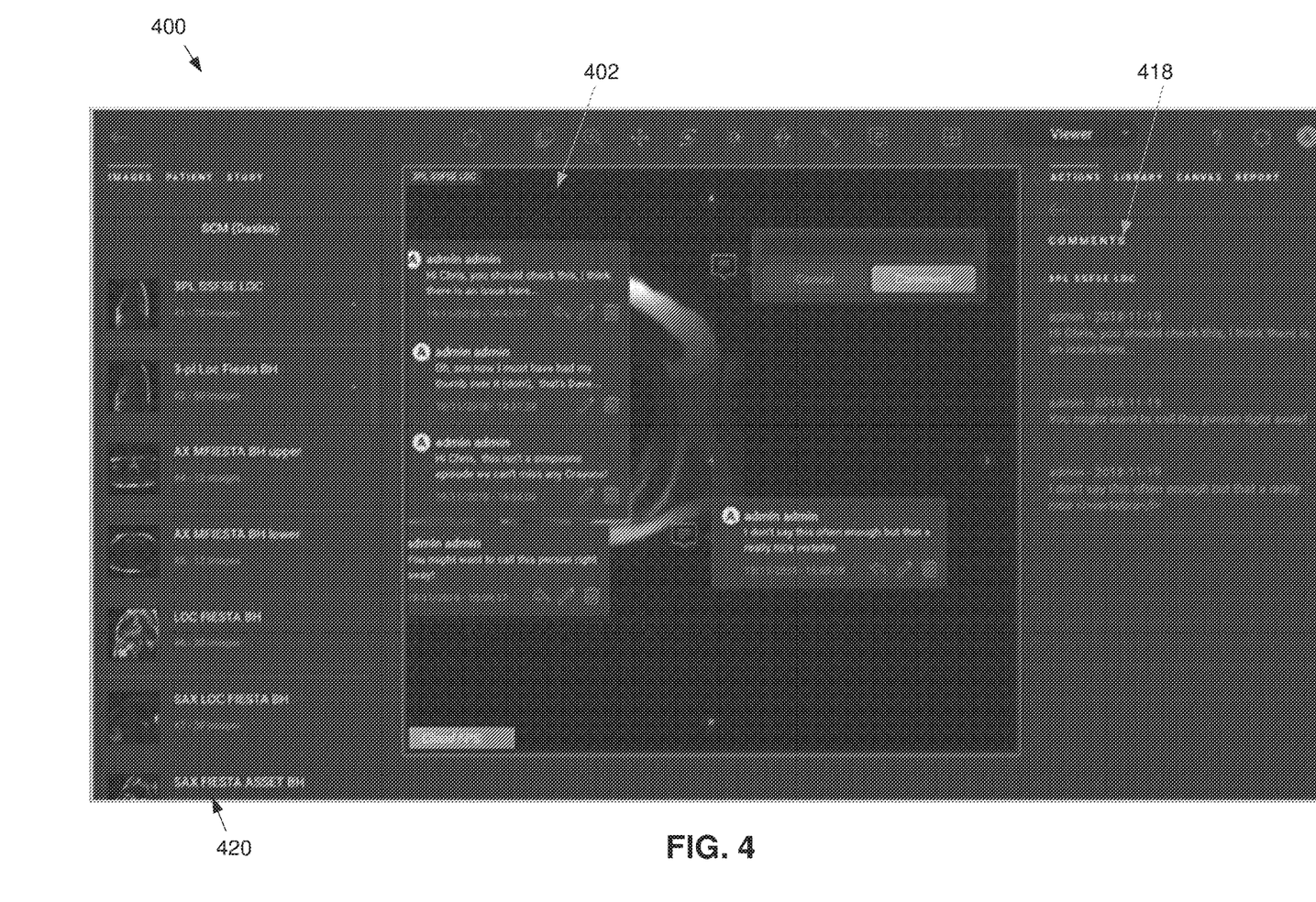
FIG. 4 shows an exemplary workspace displaying a comment list.

Referring to FIG. 4, a workspace 400 showing a comment list 418 associated with an image stack 420 is illustrated. As shown, the viewer application may display a plurality of comments in a comment list 418 associated with a plurality of image files making up an image stack 420. An image stack may refer to a collection of related DICOM image files, for example, a series of cross-sections of the heart, or a multi-modal compilation of DICOM image files.

Batch comment actions may be applied across an image stack 420, such as minimizing all comments (i.e., to their icons), hiding all comments (i.e., including icons), deleting all comments, and exporting comment information to a third-party database management system.

Selecting a comment from the comment list 418 may cause the comment information to be displayed through the viewer application, i.e., if the correct image file is displayed. If the image file corresponding to the selected comment is not already being displayed, the viewer application will first display the appropriate image file within the image stack 420 before displaying the comment thereon.

In another embodiment, a location of a placed comment may be modified by directly modifying the world coordinates associated with the placed comment. For example, a moved comment may be associated with a new location, i.e., new image coordinates. Comparing the new image coordinates with the image coordinates of the previous location, the viewer application may determine an update to the comment's world coordinates and transmit the same to the viewer system to be stored in a memory therein.

Figure 5:
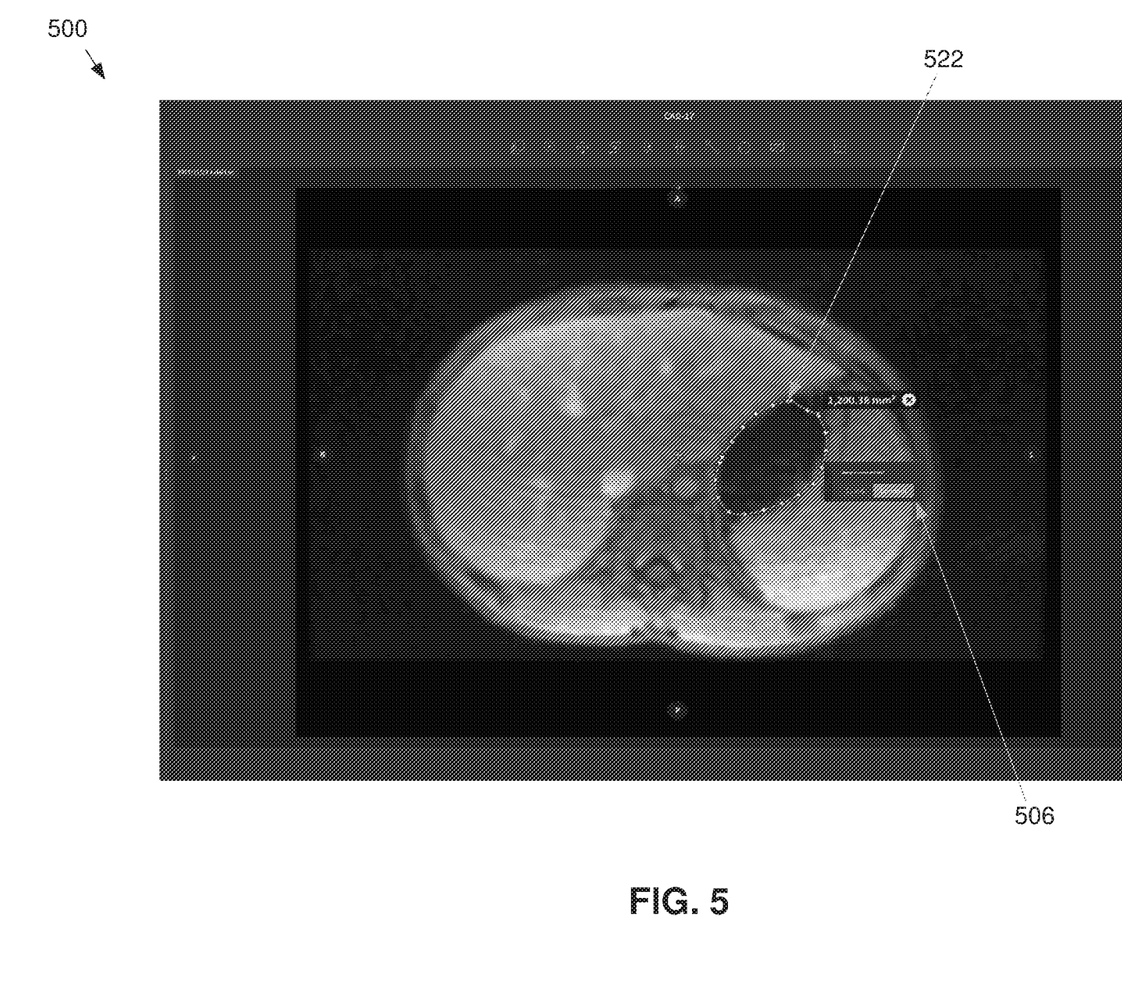
FIG. 5 shows an exemplary workspace demonstrating placement of an annotation.

Referring to FIG. 5, a workspace 500 showing placement of an annotation 522 and a comment 506 made thereon. As shown, a comment 506 may be associated with an image annotation 522, e.g., a measurement. An image annotation may be fully encoded using standard DICOM tags included in a DICOM image file. Or, the image annotation may be encoded in one or more private data elements of the DICOM image file. In yet another example, an image annotation may be a graphic annotation sequence embedded in the DICOM image or embedded in an annotation object configured to reference the annotated DICOM image file. The annotation object may comprise a graphic annotation, a pointer to the corresponding DICOM image file, and a location in the DICOM image. The location may comprise world coordinates (which are converted to image coordinates before the image is displayed by the viewer application) or image coordinates. In one embodiment, a location of a comment associated with an annotation object may be the same as the location of the annotation object. In any case, the comment additionally comprises a pointer to the measurement object (if separate from the DICOM image file) or a private data element.

In one or more embodiments, the viewer system may allow a user to create, store, and share a workspace. As used herein, 'workspace' refers to a collection of DICOM image files and one or more user interface view(s) thereof related to a study. A study may be associated with more than one workspace. The user interface(s) may be configured by a user to include annotations, comments, visual analytics, patient demographic information, or any other toolsets which may be used in the course of image analysis and collaboration with other professionals. Any such configuration of the workspace may be stored in a memory of the viewer system.

In one embodiment, a workspace may be associated with identity information. The identity information may comprise an organization ID associated with a particular organization and a name ID associated with a particular user. In one embodiment, workspace permissions may be set and subsequently modified by the workspace creator to regulate read/write access to the workspace. In a simplest use-case, an organization policy may pre-authorize all or a subset of users, e.g., assigned radiologists, to facilitate user collaboration in imaging studies.

In a preferred embodiment, an organization ID is a required attribute of a workspace. The name ID may be an optional attribute, which allows a permitted user to assume only an organizational identity, i.e., a non-user-specific workspace. For example, any users within an organization associated with an organization ID may access workspaces bearing organization ID. However, when multiple users from the same organization access an organizational workspace, only one user should be selected in order to preserve the workspace configurations. Multiple concurrent users editing a single workspace may create forks in the version history. As such, the viewer system facilitates workspace sharing by, inter alia, applying workspace locks, resolving concurrent editing and commenting, and introducing an auditing facility.

A workspace lock may be a key/value pair generated by the viewer system and stored in a database of the viewer system or a third-party data store, e.g., REDIS, MongoDB, Memcached, etc. The workspace lock key may comprise the organization ID, the name ID, and the study ID. A workspace lock value may be a stringified object having therein an app ID associated with the app ID that owns the workspace lock, an email address associated with the user whose app ID owns the workspace lock, the organization ID of the user whose app ID owns the workspace lock, and a name ID of the user whose app ID owns the workspace lock.

In one embodiment, a workspace lock acquisition method may involve receiving STUDY ID and user identity inputs from a user device. Based on the STUDY ID and user identity inputs, the viewer system may temporarily generate a session hash comprising a current workspace identifier and store the hash in memory. In a further step, the viewer system may determine one or more other workspace identifiers associated with the received STUDY ID.

In a further step, the viewer system generates a separate workspace lock for each workspace identifier associated with the received STUDY ID. The received user identity input may be utilized, or a default user identity may be relied upon by the viewer system to generate each workspace lock's corresponding key and value pair. In a separate embodiment described below, when multiple users contend over a workspace lock for the same study, the viewer system must resolve lock contention.

In a final step, the viewer system generates the workspace lock and allows the user to utilize the workspace. If the workspace lock is not acquired (i.e., if a workspace lock was already acquired by another user), the user may only view the workspace but not affect the user interfaces or layout thereof. This may occur if any workspace related to the desired study ID is currently locked (i.e., in use) by another user.

In one embodiment, the viewer system may resolve contention between workspace lock requests from different users. In a first step, a first user device may issue a first detection request to the viewer system to detect changes made to a workspace key. For example, a REDIS WATCH command may be utilized. In a second step, a second user device may issue a second detection request to the viewer system to detect changes made to the workspace lock key. In a further step, the first user transmits a first claim request to claim the workspace lock (see workspace lock acquisition method above). In another step, the second user transmits a second claim request to claim the workspace lock. In another step, if no changes have been detected by the first detection request, the viewer system processes the first claim request and transfers ownership of the workspace lock key to the first user device, i.e., the user identity associated with the first user device is applied to the workspace lock key. In a further step, the viewer system denies the second claim request (i.e., transmits a null response), on the basis that the second detection request detects the change made to the workspace lock key as a result of processing the first claim request.

In another embodiment, the viewer system is configured to prevent multiple, concurrent viewer application instances by the same user. A user may forget that an instance of the viewer application is being executed by the user device (e.g., the viewer application may be idle in a browser tab). A preferred embodiment is for the viewer system to detect a new instance executed by the user and end any previously running instances. In doing so, the viewer system reduces overall bandwidth for the viewer system and the user device and prevents concurrent changes from corrupting a workspace configuration.

This may be achieved by utilizing the app ID element of the workspace lock value. The app ID describes the context in which an instance is executed. In the event that a new instance of the viewer application is commissioned by a user device utilizing the same app ID, the viewer system may detect the same, point the workspace lock to the new instance and close the previous instance. The user interface of the previous instance may no longer display the locked workspace; optionally, a dialogue may be displayed to guide the user to the running instance, a different workspace, and/or close the existing tab.

In one embodiment, a workspace lock expires after a threshold period, such as 30 seconds. To prevent expiry, a viewer application utilized by a user device may ping the viewer system regularly to keep the connection alive. In the event that a workspace lock expires, the viewer system may proceed with a lock releasing method as described below.

In one embodiment, the viewer system may release a workspace lock when a workspace lock expires; a workspace lock may expire when, for example, a user logs out from the viewer application, or, a workspace lock may expire when the user switches to a workspace related to a different study.

In a first step, the viewer system may detect one or more of the group consisting of: a user logout event from a current workspace, and a workspace exit event from a current workspace, current workspace being associated with a workspace identifier, a STUDY ID, and the user's identity information. In a further step, the viewer system may determine one or more other workspace identifiers sharing a STUDY ID with the current workspace identifier. In a final step, the viewer system may remove all workspace locks associated with matching workspace identifiers from memory.

Figure 6:
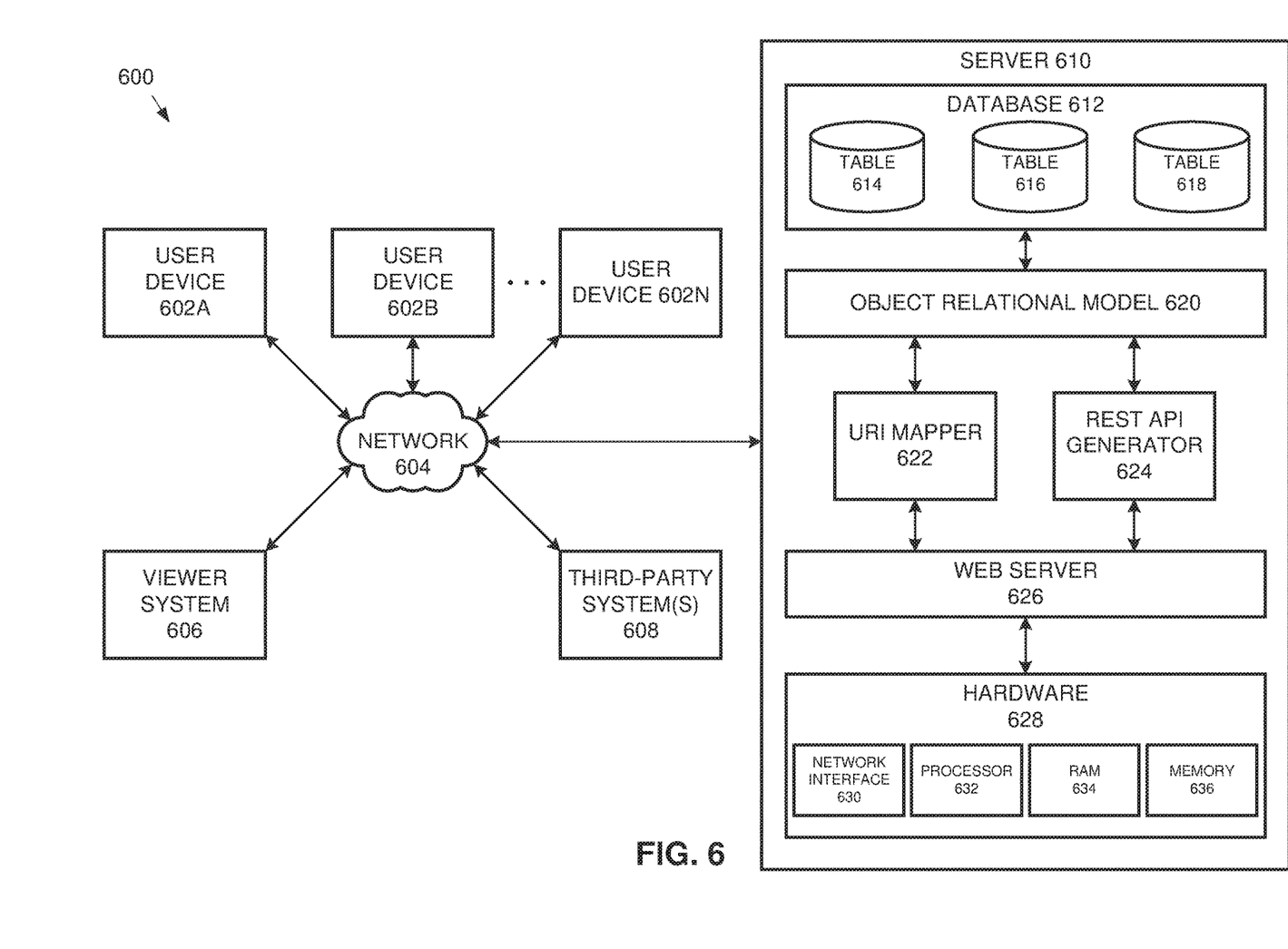
FIG. 6 shows a block diagram of an exemplary medical imaging viewer system.

Referring to FIG. 6, a block diagram showing an exemplary medical imaging viewer system 600 is illustrated. As shown, the system 600 comprises any number of user devices 602A-N capable of accessing the viewer system 606 and third party system(s) 608 through a network 604 (e.g., Internet, local area network, wide area network, cellular, intranet, etc.). The viewer system 606 may, inter alia, perform the comment creation and storage method 100 described above. Alternatively, various steps of the above method and any other methods described herein may be performed by the user device(s) 602A-N or third-party system(s) 608.

In one embodiment, the viewer system 606 may be entirely or partially implemented on one or more servers 610, comprising hardware 628 such as any number of processors 632, random-access memory (RAM) 634, and internal or external memory 636. The server 610 may include a network interface 630 such that it may access the network 604 to send or receive information through the network 604.

As shown, at least one database 612 may be accessed by the server 610. Although shown as internal to the server 610, it will be appreciated that the database 612 may be accessed by the server 610 over the network 604 or via another wired or wireless connection. The server 610 may store desired or required information in the database 612 and may access the same to retrieve the information. As shown, the database 612 may include one or more database tables 614-618.

The database 612 may be in communication with an object relational mapping (ORM) tool, also known as an object relational model 620 or object-relational database management system. Although shown as internal to the server 610, it will be appreciated that the ORM 620 may be accessed by the server 610 over the network 604 or via physical connection.

The ORM 620 may be in communication with one or more of the following: a Universal Resource Indicator (URI) mapper 622, and a Rest API generator 624. First, the URI mapper 622 may map a URI into a pointer to an internal program, view, logic, or presentation of data within the system, based on one or more rules of a matching object specified in a collection of mapping objects. The matching object may be a regular expression. The URI mapper 622 may be in communication with a web server 626.

The Rest API generator 624 may be in communication with a web server to send and/or receive data to/from user devices communicating with the server 610 using HTTP and/or HTTPS. The Rest API generator 624 may prepare data stored in the database 612 for delivery to a user device, may receive data from connected systems and/or may prepare data received for storage or transmission to one or more connected systems. The Rest API generator 624 may be capable of translating between formats including, but not limited to, JSON, DICOM, XML, CSV, and the like. The Rest API generator 624 may be capable of automatically generating URIs based upon data structures observed in the ORM 620 for access by client devices and connected systems.

A web server 626 may be adapted to deliver web pages on request to user devices using the Hypertext Transfer Protocol (HTTP and/or HTTPS) or similar protocols. This allows for delivery of HTML documents and any additional content that may be included by a document, such as images, style sheets and scripts.

A user device 602A-N may employ a web browser or similar client application to engage in communication with a web server. For example, a client application may make a request for a specific resource using HTTP/HTTPS and the web server may respond with the content of that resource or an error message if unable to do so. The resource may be data or a file stored in a database. The web server can receive content from a user device, possibly using HTTP/HTTPS.

In certain embodiments, a user device 602A-N may access the server 610 (i.e., an application running on the server) through a network 604. The user device may be capable of running a client application or other software, like a web browser or web-browser-like application (e.g., a viewer application). In one embodiment, the user device 602A-N may comprise, for example, an input/output device, a display, a processor, memory, and/or audio equipment. Exemplary user devices include, but are not limited to, general purpose computers, laptops, cell phones, smartphones, personal digital assistants, televisions, tablets, wearable devices and the like.

An exemplary viewer application may comprise HTML data, images, icons, and/or executable code. The executable code may be composed in JavaScript, ECMAscript, coffeescript, python, Ruby or other programming languages suitable for execution within the client application, or translation into a client application executable form.

It will be apparent to one with ordinary skill in the art that, in certain embodiments, any of the functionality of the user device 602A-N, viewer system 606, and third-party system(s) 608 may be incorporated into the server 610, and vice versa. Likewise, any functionality of a viewer application may be incorporated into a browser-based client, and such embodiments are intended to be fully within the scope of the disclosure.

In one embodiment, communication between a viewer system and a connected device or system may involve the use of a translation and/or serialization module. A serialization module can convert an object from an in-memory representation to a serialized representation suitable for transmission via HTTP or another transport mechanism. For example, the serialization module may convert data from a native Python, Ruby, or Java in-memory representation into a JSON string for communication over the client-to-server transport protocol.

Embodiments of the subject matter and the functional operations described in this specification can be implemented in one or more of the following: digital electronic circuitry; tangibly-embodied computer software or firmware; computer hardware, including the structures disclosed in this specification and their structural equivalents; and combinations thereof. Such embodiments can be implemented as one or more modules of computer program instructions encoded on a tangible non-transitory program carrier for execution by, or to control the operation of, data processing apparatus (i.e., one or more computer programs). Program instructions may be, alternatively or additionally, encoded on an artificially generated propagated signal (e.g., a machine-generated electrical, optical, or electromagnetic signal) that is generated to encode information for transmission to suitable receiver apparatus for execution by a data processing apparatus. And the computer storage medium can be one or more of: a machine-readable storage device, a machine-readable storage substrate, a random or serial access memory device, and combinations thereof.

As used herein, the term "data processing apparatus" comprises all kinds of apparatuses, devices, and machines for processing data, including but not limited to, a programmable processor, a computer, and/or multiple processors or computers. Exemplary apparatuses may include special purpose logic circuitry, such as a field programmable gate array (FPGA) and/or an application specific integrated circuit (ASIC). In addition to hardware, exemplary apparatuses may comprise code that creates an execution environment for the computer program (e.g., code that constitutes one or more of: processor firmware, a protocol stack, a database management system, an operating system, and a combination thereof).

The term "computer program" may also be referred to or described herein as a "program," "software," a "software application," a "module," a "software module," a "script," or simply as "code." A computer program may be written in any form of programming language, including compiled or interpreted languages, or declarative or procedural languages, and it can be deployed in any form, including as a standalone program or as a module, component, subroutine, or other unit suitable for use in a computing environment. Such software may correspond to a file in a file system. A program can be stored in a portion of a file that holds other programs or data. For example, a program may include one or more scripts stored in a markup language document; in a single file dedicated to the program in question; or in multiple coordinated files (e.g., files that store one or more modules, sub programs, or portions of code). A computer program can be deployed and/or executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, such as but not limited to, an FPGA and/or an ASIC.

Computers suitable for the execution of the one or more computer programs include, but are not limited to, general purpose microprocessors, special purpose microprocessors, and/or any other kind of central processing unit (CPU). Generally, CPU will receive instructions and data from a read only memory (ROM) and/or a RAM. The essential elements of a computer are a CPU for performing or executing instructions and one or more memory devices for storing instructions and data. Generally, a computer will also include, or be operatively coupled to receive data from or transfer data to, or both, one or more mass storage devices for storing data (e.g., magnetic, magneto optical disks, and/or optical disks). However, a computer need not have such devices. Moreover, a computer may be embedded in another device, such as but not limited to, a mobile telephone, a personal digital assistant (PDA), a mobile audio or video player, a game console, a Global Positioning System (GPS) receiver, or a portable storage device (e.g., a universal serial bus (USB) flash drive).

Computer readable media suitable for storing computer program instructions and data include all forms of nonvolatile memory, media and memory devices. For example, computer readable media may include one or more of the following: semiconductor memory devices, such as erasable programmable read-only memory (EPROM), electrically erasable programmable read-only memory (EEPROM) and/or flash memory devices; magnetic disks, such as internal hard disks or removable disks; magneto optical disks; and/or CD ROM and DVD-ROM disks. The processor and the memory can be supplemented by, or incorporated in, special purpose logic circuitry.

To provide for interaction with a user, embodiments may be implemented on a computer having any type of display device for displaying information to a user. Exemplary display devices include, but are not limited to one or more of: projectors, cathode ray tube (CRT) monitors, liquid crystal displays (LCD), light-emitting diode (LED) monitors and/or organic light-emitting diode (OLED) monitors. The computer may further comprise one or more input devices by which the user can provide input to the computer. Input devices may comprise one or more of: keyboards, a pointing device (e.g., a mouse or a trackball). Input from the user can be received in any form, including acoustic, speech, or tactile input. Moreover, feedback may be provided to the user via any form of sensory feedback (e.g., visual feedback, auditory feedback, or tactile feedback). A computer can interact with a user by sending documents to and receiving documents from a device that is used by the user (e.g., by sending web pages to a web browser on a user's device in response to requests received from the web browser).

Embodiments of the subject matter described in this specification can be implemented in a computing system that includes one or more of the following components: a backend component (e.g., a data server); a middleware component (e.g., an application server); a frontend component (e.g., a client computer having a graphical user interface (GUI) and/or a web browser through which a user can interact with an implementation of the subject matter described in this specification); and/or combinations thereof. The components of the system can be interconnected by any form or medium of digital data communication, such as but not limited to, a communication network. Non-limiting examples of communication networks include a local area network (LAN) and a wide area network (WAN), e.g., the Internet.

The computing system may include clients and/or servers. The client and server may be remote from each other and interact through a communication network. The relationship of client and server arises by virtue of computer programs running on the respective computers and having a client-server relationship to each other.

Various embodiments are described in this specification, with reference to the detailed description above, the accompanying drawings, and the claims. Numerous specific details are described to provide a thorough understanding of various embodiments. However, in certain instances, well-known or conventional details are not described in order to provide a concise discussion. The figures are not necessarily to scale, and some features may be exaggerated or minimized to show details of particular components. Therefore, specific structural and functional details disclosed herein are not to be interpreted as limiting, but merely as a basis for the claims and as a representative basis for teaching one skilled in the art to variously employ the embodiments.

The embodiments described and claimed herein and drawings are illustrative and are not to be construed as limiting the embodiments. The subject matter of this specification is not to be limited in scope by the specific examples, as these examples are intended as illustrations of several aspects of the embodiments. Any equivalent examples are intended to be within the scope of the specification. Indeed, various modifications of the disclosed embodiments in addition to those shown and described herein will become apparent to those skilled in the art, and such modifications are also intended to fall within the scope of the appended claims.

While this specification contains many specific implementation details, these should not be construed as limitations on the scope of any disclosure or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous.

Moreover, the separation of various system modules and components in the embodiments described above should not be understood as requiring such separation in all embodiments, and it should be understood that the described program components and systems can generally be integrated together in a single software product or packaged into multiple software products.

All references including patents, patent applications and publications cited herein are incorporated herein by reference in their entirety and for all purposes to the same extent as if each individual publication or patent or patent application was specifically and individually indicated to be incorporated by reference in its entirety for all purposes.

The invention claimed is:

1. A method of incorporating a comment within a Digital Imaging and Communications in Medicine (DICOM) image file, comprising:
  receiving, by a processor of an image viewer system, a comment location of a medical image of the DICOM image file and comment information associated with the comment from a user device associated with a user, wherein the comment location comprises image coordinates relative to a viewer application executed on the user device, and
    wherein the comment information comprises a text body, identity information related to the user, and a comment creation date; and
  standardizing an incorporation of the comment with the DICOM image file in accordance with one or more DICOM standards by at least;
    converting the image coordinates relative to the viewer application into world coordinates associated with the image viewer system, wherein the world coordinates are convertible to other image coordinates relative to another viewer application when the image is presented via the other viewer application to display the comment at the comment location; and
    storing, in a storage medium of the image viewer system, the world coordinates and the comment information as a subset of one or more header attributes of the DICOM image file, wherein the one or more header attributes are preserved according to the one or more DICOM standards as one or more modality-specific attributes to provide future reference for information retrieval.

2. The method of claim 1, further comprising:
receiving an edit request from the user device to modify the text body of the comment.

3. The method of claim 1, further comprising:
receiving a move request comprising updated image coordinates from the user device to modify the world coordinates accordingly.

4. The method of claim 1, further comprising:
receiving a pin request to prevent the comment location from being modified.

5. The method of claim 1, further comprising:
receiving a reply to the comment from another user device of another user, reply being associated with the comment location and comprising a reply text body, identity information related to the other user, and a reply creation date.

6. The method of claim 5, wherein the comment and the reply are stored in the one or more header attribute(s) and are threaded based on corresponding creation dates.

7. The method of claim 1, wherein the comment shares image coordinates with an annotation object associated with the DICOM image file.

8. The method of claim 1, wherein the DICOM image file comprises a plurality of DICOM images.

9. The method of claim 1, wherein one of the one or more header attributes is a study ID attribute.

10. A method of claiming access to a workspace in a Digital Imagine and Communications in Medicine (DICOM) imaging environment, comprising:
   receiving, by a processor of an image viewer system, a study ID related to a medical imaging study and a user identity from a user device associated with a user, wherein the user identity comprises one or more of the group consisting of: an organization ID, a name ID, an app ID, and an email address;
   generating a session hash comprising a workspace identifier associated with the study ID and the user identity; and
   storing the session hash in memory to further generate at least one workspace lock for resolving concurrent access to the workspace by the user and one or more other users, wherein the workspace includes a collection of DICOM image files and one or more user interface views associated with the medical imaging study.

11. The method of claim 10, further comprising:
   determining one or more other workspace identifiers associated with the same study ID;
   generating one or more workspace locks each comprising a key-value pair, including a workspace key and a workspace value, for an individual workspace identifier determined to be associated with the study ID,
      wherein the workspace key comprises an organization ID, a name ID, and the study ID, and
      wherein the workspace value comprises the app ID, the email address, the organization ID, and the name ID; and
   storing the workspace lock(s) in memory.

12. The method of claim 11, wherein the one or more workspace locks are configured to expire after a preconfigured period in which a 'stay alive' request is not received by the image viewer system from the user device.

13. The method of claim 11, further comprising:
   detecting at least one of:
      a user logout event from the workspace, and
      a workspace exit event from the workspace; and
   removing the one or more workspace locks associated with the one or more other workspace identifiers.

14. The method of claim 11, further comprising:
   receiving a first detection request from the user device to detect changes made to the workspace key;
   receiving a second detection request from another user device;
   receiving a first claim request from the user device to apply the user identity of the user to the workspace key;
   receiving a second claim request from the other user device;
   writing the user identity of the user to the workspace key and transmitting a confirmation in response to the first claim request; and
   upon the second detection request detecting a change to the workspace key, transmitting a null response to the second claim request.

15. The method of claim 11, wherein the generating comprises detecting another workspace identifier stored in the memory of the image viewer system sharing an app ID with the workspace identifier, wherein the other workspace identifier is associated with a previously running workspace instance.

16. The method of claim 15, further comprising terminating the previously running instance.

* * * * *